US010966915B2

(12) United States Patent
Sturgis et al.

(10) Patent No.: US 10,966,915 B2
(45) Date of Patent: *Apr. 6, 2021

(54) DEODORANT COMPOSITIONS

(71) Applicant: The Procter & Gamble Company, Cincinnati, OH (US)

(72) Inventors: David Arthur Sturgis, Montgomery, OH (US); Lindsey Michelle Britt, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/716,542

(22) Filed: Dec. 17, 2019

(65) Prior Publication Data

US 2020/0129415 A1 Apr. 30, 2020

Related U.S. Application Data

(63) Continuation of application No. 16/021,965, filed on Jun. 28, 2018, now Pat. No. 10,543,164.

(60) Provisional application No. 62/647,104, filed on Mar. 23, 2018, provisional application No. 62/527,180, filed on Jun. 30, 2017.

(51) Int. Cl.
*A61K 8/92* (2006.01)
*A61Q 15/00* (2006.01)
*A61K 8/19* (2006.01)
*A61K 8/02* (2006.01)
*A61Q 17/00* (2006.01)
*A61K 8/73* (2006.01)
*A61K 8/37* (2006.01)
*A61K 8/49* (2006.01)

(52) U.S. Cl.
CPC .............. *A61K 8/92* (2013.01); *A61K 8/0229* (2013.01); *A61K 8/0241* (2013.01); *A61K 8/19* (2013.01); *A61K 8/37* (2013.01); *A61K 8/375* (2013.01); *A61K 8/4926* (2013.01); *A61K 8/732* (2013.01); *A61K 8/922* (2013.01); *A61Q 15/00* (2013.01); *A61K 2800/30* (2013.01); *A61K 2800/34* (2013.01); *A61K 2800/74* (2013.01); *A61Q 17/005* (2013.01)

(58) Field of Classification Search
None
See application file for complete search history.

(56) References Cited

U.S. PATENT DOCUMENTS

| 3,792,068 | A | 2/1974 | Luedders |
| 3,887,692 | A | 6/1975 | Gilman |
| 3,904,741 | A | 9/1975 | Jones |
| 4,049,792 | A | 9/1977 | Elsnau |
| 4,120,948 | A | 10/1978 | Shelton |
| 4,359,456 | A | 11/1982 | Gosling |
| 4,906,454 | A | 3/1990 | Melanson, Jr. |
| 5,019,375 | A | 5/1991 | Tanner et al. |
| 5,298,640 | A | 3/1994 | Callaghan |
| 5,429,816 | A | 7/1995 | Hofrichter et al. |
| 5,675,013 | A | 10/1997 | Hani |
| 5,744,146 | A | 4/1998 | Peters |
| 5,891,424 | A | 4/1999 | Bretzler et al. |
| 5,972,319 | A | 10/1999 | Linn et al. |
| 5,976,514 | A | 11/1999 | Guskey et al. |
| 6,177,066 | B1 | 1/2001 | Pataut |
| 6,485,717 | B1 * | 11/2002 | Scavone ............... A61K 8/11 424/400 |
| 6,503,944 | B1 | 1/2003 | Chanchani |
| 6,624,126 | B1 | 9/2003 | Kasuga et al. |
| 7,033,576 | B2 | 4/2006 | Chevallier |
| 7,033,579 | B1 * | 4/2006 | Scavone ............... A61K 8/02 424/400 |
| 7,425,321 | B2 | 9/2008 | Lemoine |
| 8,460,720 | B2 | 6/2013 | Bergeron et al. |
| 8,574,559 | B2 | 11/2013 | Banowski |
| 9,468,596 | B2 | 10/2016 | Eizen |
| 9,517,193 | B2 | 12/2016 | Fares |
| 9,949,920 | B2 | 4/2018 | Hakim |
| 10,543,164 | B2 * | 1/2020 | Sturgis ............... A61K 8/0241 |
| 10,555,884 | B2 | 2/2020 | Sturgis |
| 2001/0046479 | A1 | 11/2001 | Landa |
| 2002/0086039 | A1 * | 7/2002 | Lee ..................... C03C 3/097 424/401 |
| 2003/0235546 | A1 | 12/2003 | Mattai et al. |
| 2005/0281767 | A1 | 12/2005 | Walling et al. |

(Continued)

FOREIGN PATENT DOCUMENTS

| BE | 825146 A1 | 8/1975 |
| GB | 2048229 A | 12/1980 |

(Continued)

OTHER PUBLICATIONS

International Search Report; International Application No. PCT/US2019/022660; dated Jun. 4, 2019; 14 pages.
International Journal Cosmetic Science, 2003, 25, pp. 127-135—Iron Sequestration on Skin: A New Route to Improved Deodorancy.
Nivea Fresh Natural Deodorant, pulled from the Internet (www.GNPD.com) 3 pages.
International Search Report; International Application No. PCT/US2018/039972; dated Mar. 25, 2019; 10 pages.

(Continued)

Primary Examiner — Melissa S Mercier
(74) Attorney, Agent, or Firm — Kathleen Y. Carter

(57) ABSTRACT

A deodorant stick comprising: at least about 25% of a liquid triglyceride; at least one antimicrobial; a primary structurant with a melting point of at least about 50° C.; and less than 8% of secondary structurants having a melting point of at least about 60° C.; said stick being free of an aluminum salt; and said stick having a hardness from about 80 mm*10 to about 140 mm*10, as measured by penetration with ASTM D-1321 needle.

15 Claims, No Drawings

(56) References Cited

U.S. PATENT DOCUMENTS

| | | |
|---|---|---|
| 2007/0003499 A1 | 1/2007 | Shen |
| 2007/0203240 A1* | 8/2007 | Oblong .................... A61K 8/43 514/561 |
| 2011/0076309 A1 | 3/2011 | Misner |
| 2013/0045907 A1 | 2/2013 | Lanzalaco |
| 2013/0045910 A1 | 2/2013 | Miracle |
| 2014/0154189 A1 | 6/2014 | Polson et al. |
| 2015/0196477 A1 | 7/2015 | Stark |
| 2016/0074300 A1 | 3/2016 | Salvador |
| 2016/0235661 A1 | 8/2016 | Changoer et al. |
| 2016/0326091 A1 | 11/2016 | Rudolph |
| 2017/0172873 A1 | 6/2017 | Banowski |
| 2017/0252288 A1 | 9/2017 | Lesniak |
| 2019/0000730 A1 | 1/2019 | Abuelhaiga et al. |
| 2019/0000734 A1 | 1/2019 | Sturgis |
| 2019/0000736 A1 | 1/2019 | Sturgis |
| 2019/0000747 A1 | 1/2019 | Sturgis et al. |
| 2019/0276389 A1 | 9/2019 | Wos |
| 2020/0000694 A9 | 1/2020 | Sturgis |
| 2020/0214957 A1 | 7/2020 | Sturgis |

FOREIGN PATENT DOCUMENTS

| | | |
|---|---|---|
| GB | 1347950 A | 3/1985 |
| GB | 2144992 A | 3/1985 |
| JP | 2008110999 A | 5/2008 |
| WO | 2004089092 A1 | 10/2004 |
| WO | 2014139449 A1 | 9/2014 |

OTHER PUBLICATIONS

Kontoghiorghes, George J., "2-Hydroxypyridine-N-Oxides: Effective New Chelators in Iron Mobilisation", Biochimica et Biophysica Acta, vol. 924, No. 1, Apr. 16, 1987, pp. 13-18.

* cited by examiner

DEODORANT COMPOSITIONS

CROSS REFERENCE TO RELATED APPLICATIONS

This application is a continuation of U.S. patent application Ser. No. 16/021,965, filed Jun. 28, 2018, which claims the benefit of U.S. Provisional Application No. 62/527,180, filed Jun. 30, 2017, and of U.S. Provisional Application No. 62/647,104, filed Mar. 23, 2018.

FIELD OF THE INVENTION

The present disclosure relates to deodorant compositions and methods relating thereto.

BACKGROUND OF THE INVENTION

Many consumers are seeking more natural, aluminum-free deodorant offerings, often mostly free of silicones. Consumers also want a good glide, non-sticky, and non-greasy application. This is a challenge, because a mostly silicone-free formula will often use natural oils or natural oil-based triglycerides. But often natural oils, such as coconut oil, bring a large portion of wax with them, often making the resulting deodorant sticks too hard to meet a more preferable product application for both shaven and unshaven underarms. They are also often undesirably greasy due to the non-volatile nature.

Thus there remains a challenge to formulate an aluminum-free, mostly silicone-free deodorant stick that is not too hard.

SUMMARY OF THE INVENTION

A deodorant stick comprising: at least about 25% of a liquid triglyceride; at least one antimicrobial; a primary structurant with a melting point at least about 50° C.; and less than 8% of secondary structurants having a melting point of at least about 60° C.; said stick being free of an aluminum salt; and said stick having a hardness from about 80 mm*10 to about 140 mm*10, as measured by penetration with ASTM D-1321 needle.

DETAILED DESCRIPTION OF THE INVENTION

While the specification concludes with claims that particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term "anhydrous" as used herein means substantially free of added or free water. From a formulation standpoint, this means that the anhydrous deodorant stick compositions of the present invention contain less than about 1%, and more specifically zero percent, by weight of free or added water, other than the water of hydration typically associated with the particulate deodorant active prior to formulation.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "majority" refers to greater than about 51% of the stated component or parameter.

"Substantially free of" refers to about 2% or less, about 1% or less, or about 0.1% or less of a stated ingredient. "Free of" refers to no detectable amount of the stated ingredient or thing.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

As consumers seek more natural ingredients in their deodorants, one approach to formulation is to use emollients derived from natural oils. Emollients derived from natural oils are derived from plant sources, such as palm oil or coconut oil. One example of an emollient derived from natural oils may be a liquid triglyceride, defined as liquid at 25° C. Thus, products that hope to emphasize natural ingredients may have a significant amount of a liquid triglyceride, for example.

In order to provide structure to the deodorant stick composition, the formulation may also include a number of waxes and other structurants. However, the structurants used may lead to deodorant sticks that are very hard. For example, a currently marketed product, Comparative Formula 1 below, has 34.15% liquid triglyceride, along with a number of structurants, resulting in a very hard stick, scoring 63 on a needle penetration test under ASTM D-1321 (as described herein). So while Comparative Formula 1 uses consumer-preferred natural ingredients, it does not necessarily provide a good consumer experience when used, given its hardness. Comparative Formula 2 contains even higher levels of structurants, resulting in a harder stick with an even lower hardness score. In comparison, Inventive Examples 1-5, while comprising consumer-preferred natural ingredients, have higher hardness scores, meaning they are softer products.

The primary structurant in the present invention may have a melting point of at least about 50° C., in some embodiments from about 50° C. to about 70° C., and in other embodiments from about 50° C. to about 75° C., and in other embodiments from about 60° C. to 80° C. A primary structurant is defined as the structurant that is present in the composition in the greatest amount (liquid triglycerides are not considered a structurant in this context). Some embodiments may have just a single structurant, so may have only a primary structurant. Other embodiments may have a primary structurant and then secondary structurants, those structurants that are used in a lesser amount than the primary structurant.

The primary structurant may comprise from about 5% to about 20%, in some cases 7-17% of the deodorant stick. The secondary structurants may cumulatively comprise about 12% or less, or about 8% or less of the deodorant stick, in

TABLE 1

|  | Comparative Formula 1 | Comparative Formula 2 | Inventive Example 1 | Inventive Example 2 | Inventive Example 3 | Inventive Example 4 | Inventive Example 5 |
| --- | --- | --- | --- | --- | --- | --- | --- |
| Hardness (Penetration mm*10) | 63 | 56 | 97 | 90 | 117 | 86 | 85 |
| Caprylic/Capric Triglyceride | 34.15 | 31.15 | 43.4 | 44.7 | 42.7 | 46.9 | 46.15 |
| Arrowroot Powder | 23 | 23 | 19 | 23 | 23 | 19 |  |
| Stearyl Alcohol | 12 | 12 | 11.5 | 10.7 | 10.7 |  |  |
| Ozokerite |  |  |  |  | 1.5 | 11 | 11.75 |
| Castor Wax | 3 | 4 | 3 | 3 | 3 |  |  |
| Baking Soda | 12 | 12 | 12 | 12 | 6 | 6 |  |
| Magnesium Hydroxide |  |  |  |  | 6 | 6 | 12.0 |
| Shea Butter | 6 | 6 | 2 | 2 | 2 | 2 | 2 |
| Coconut Oil | 4.75 | 4.75 | 4.5 | 4.5 | 4.5 | 4.5 | 4.5 |
| Polyglycerol-3 Beeswax | 2.5 | 3.5 |  |  |  |  |  |
| Jojoba Esters 70 | 1 | 2 |  |  |  |  |  |
| Glyceryl Caprylate (and) Glyceryl Undecylenate | 1 | 1 |  |  |  |  |  |
| Perfumes | 0.6 | 0.6 | 0.6 | 0.6 | 0.6 | 0.6 | 0.6 |
| Cyclodextrin |  |  | 4 |  |  | 4 | 4 |
| Tapioca Starch |  |  |  |  |  |  | 19.0 |

It is known that to formulate a solid antiperspirant or deodorant stick, the structurants generally have a melting point above 50° C. to provide a stable structure to the stick. The present inventors have discovered that a deodorant stick having at least about 25% of a liquid triglyceride, and that uses a primary structurant that has a melting point of at least about 50° C., in some embodiments from about 50° C. to 70° C. and in still other embodiments from about 50° C. to about 75° C., while limiting the amount of secondary structurants having a melting point of at least about 60° C. to 8% or less, can result in a deodorant stick with a hardness from about 80 mm*10 to about 140 mm*10. Such a deodorant stick is able to comprise consumer-perceived natural ingredients, while offering a pleasant consumer experience in terms of its hardness.

A. Structurants

The deodorant compositions of the present invention comprise a suitable concentration of structurants to help provide the compositions with the desired viscosity, rheology, texture and/or product hardness, or to otherwise help suspend any dispersed solids or liquids within the composition.

some embodiments less than about 5%, less than about 3%, or less than about 1% of the deodorant stick. In some embodiments, the deodorant stick may be free of or substantially free of any secondary structurants In some embodiments, some secondary structurants may have a melting point less than 60° C., and then remaining secondary structurants have a melting point of at least about 60° C. The percentage of secondary structurants having a melting point less than 60° C. may not be as significant as the percentage of secondary structurants having a melting point of at least about 60° C., as the higher melting structurants are what contribute more to the hardness of the deodorant stick. So in some embodiments, the secondary structurants having a melting point of at least about 60° C. may cumulatively comprise 8% or less of the deodorant stick, in some embodiments less than about 5% of the deodorant stick, less than about 3% of the deodorant stick, or less than about 1% of the deodorant stick. In some embodiments, the deodorant stick may be free of or substantially free of any secondary structurants having a melting point of at least about 60° C.

The term "structurant" as used herein means any material known or otherwise effective in providing suspending, gelling, viscosifying, solidifying, and/or thickening properties to the composition or which otherwise provide structure to the final product form.

Waxes with melting points between 50° C. and 70° C. include Japan wax, lemon wax, grapefruit wax, beeswax, ceresine, paraffin, hydrogenated jojoba, ethylene glycol distearate, stearyl stearate, palmityl stearate, stearyl behenate, cetearyl behenate, hydrogenated high erucic acid rapeseed oil, and stearyl alcohol.

Waxes with melting points above 70° C. include ozokerite, candelilla, carnauba, espartograss, cork wax, guaruma, rice oil wax, sugar cane wax, ouricury, montan ester wax, sunflower wax, shellac, ozocerite, microcrystalline wax, sasol wax, polyethylenes, polymethylenes, ethylene glycol dipalmitate, ethylene glycol di(12-hydroxystearate), behenyl behenate, glyceryl tribehenate, hydrogenated castor oil (castor wax), and behenyl alcohol.

Waxes with melting points that could vary and possibly fall into either of the two previous groups (depending on factors such as chain length) include C18-C36 triglyceride, Fischer-Tropsch waxes, silicone waxes, C30-50 alkyl beeswax, C20-40 alkyl erucates, C18-38 alkyl hydroxy stearoyl stearates, C20-40 dialkyl esters of dimer acids, C16-40 alkyl stearates, C20-40 alkyl stearates, cetyl ester wax, and spermaceti.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the deodorant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; solid triglycerides; behenyl alcohol, or combinations thereof. The deodorant stick may further comprise one or more structural elements selected from the group consisting of waxes, natural oils, coconut oil, fractionated coconut oil, jojoba seed oil, olive oil, soybean oil, sunflower oil, and combinations thereof.

Other non-limiting examples of primary structurants suitable for use herein are described in U.S. Pat. No. 5,976,514 (Guskey et al.) and U.S. Pat. No. 5,891,424 (Bretzler et al.), the descriptions of which are incorporated herein by reference.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. No. 5,976,514 (Guskey et al.) and U.S. Pat. No. 5,891,424 (Bretzler et al.).

B. Emollients

As discussed, an effective and consumer-preferred emollient may be a liquid triglyceride. Derived directly from plant sources, they are often short chains. Longer chain triglycerides may be used as structurants in deodorant or antiperspirant sticks, but the triglycerides of the present invention are liquid at room temperature (25° C.) and tend to be shorter chains. An example may be caprylic/capric triglyceride (coconut oil fractionated).

The present inventive deodorant sticks may comprise at least about 25% of one or more liquid triglyceride, in some embodiments, at least about 30%, at least 35%, at least about 40%, at least about 45%, or at least about 50% liquid triglyceride, by weight of the composition. In some embodiments, the deodorant stick comprises from about 25% to about 60%, by weight of the composition, of one or more liquid triglyceride, from about 25% to about 50%, from about 30% to about 50%, from about 35% to about 60%, from about 35% to about 50%, from about 40% to about 60%, or from about 40% to about 50%, by weight of the composition, of one or more liquid triglyceride. In general, the greater amount of liquid in the formulation, the softer the deodorant stick may be. The more solids in the formulation leads to greater hardness. Because achieving a sufficient softness in a deodorant stick with natural ingredients can be a challenge, it can be beneficial to formulate with higher amounts of liquids such as liquid triglyceride. The level of liquid triglyceride as referred to herein may be the sum total of one or more types of liquid triglyceride in a particular deodorant stick.

In some embodiments, additional emollients may be used, such as plant oils (generally used at less than 10%) including olive oil, coconut oil, sunflower seed oil, jojoba seed oil, avocado oil, canola oil, and corn oil. Additional emollients including mineral oil; shea butter, PPG-14 butyl ether; isopropyl myristate; petrolatum; butyl stearate; cetyl octanoate; butyl myristate; myristyl myristate; C12-15 alkylbenzoate (e.g., Finsolv™); octyldodecanol; isostearyl isostearate; octododecyl benzoate; isostearyl lactate; isostearyl palmitate; isobutyl stearate; dimethicone, and any mixtures thereof.

C. Antimicrobials

The present invention may include one or more antimicrobial compositions. For example, antimicrobials may include, without being limited to, baking soda, hexamidine, magnesium carbonate, zinc carbonate, thymol, magnesium hydroxide, magnesium hydroxide and magnesium carbonate hydroxide (dead sea salt), partially carbonated magnesium hydroxide, sodium carbonate, calcium carbonate, magnesium carbonate hydroxide, cinnamon essential oil, cinnamon bark essential oil, cinnamic aldehyde, polyvinyl formate, salycilic acid, niacinamide, phenoxyethanol, eugenol, linolenic acid, dimethyl succinate, citral, triethyl citrate, sepiwhite, an substituted or unsubstituted 2-pyridinol-N-oxide material (piroctone olamine), and combinations thereof. The deodorant stick may be free of or substantially free of a substituted or unsubstituted 2-pyridinol-N-oxide material.

In general, the total amount of antimicrobial used in the present invention may be from about 0.1% to about 30%, by weight, of the deodorant. Some antimicrobials may be used in amounts as low as about 0.1%, by weight of the deodorant stick, such as if using piroctone olamine or hexamidine as the primary antimicrobial, while others could be as high as about 25% if using magnesium hydroxide or magnesium hydroxide and magnesium carbonate hydroxide as the primary antimicrobial (primary antimicrobial being the antimicrobial present in the composition in the highest amount). In the latter cases, baking soda might still be used at a lower level, such as from about 0.1% to about 6%, as a secondary antimicrobial, or not at all.

Any of the antimicrobials of the present invention may be used as powders. It is believed that antimicrobial powders may provide a better deposition and have more longevity on the skin than antimicrobials delivered in a different form. In addition, it is believed that antimicrobial powders of a certain average particle size, typically from about 1 micron to about 5 microns, may provide a significant increase in antimicrobial efficacy.

Many antimicrobials can be effective at minimizing the skin surface bacteria. However, as a leave-on product where odor may not occur until later, even hours after application, deodorant antimicrobials are needed that will be effective for long periods of time. So while deodorant antimicrobials may be effective immediately upon application on the skin, it is believed that odor comes back quickly because the bacteria living around the hair follicle can quickly repopulate the skin surface bacteria. Historical approaches using high skin penetrating liquid antimicrobials to affect this region (for example, hexanediol) can cause irritation. Therefore, the present invention may target methods and mechanisms that can more effectively deliver antimicrobials not only to the skin surface, but to the bacteria in and around the hair follicle. While not wanting to be bound to the theory, the inventors of the present inventor believe that powders, specifically powders with an average particle size of less than about 10 microns, in some cases from about 1 micron to about 5 microns, are more efficient at getting into the hair follicle where the bacteria live and repopulate the skin surface. In some embodiments, the antimicrobials may be a combination of larger sized particles and smaller particles that are from 1 to 10 microns. As noted above, solids such as powders can impact the overall hardness of the deodorant stick. In general, greater amounts of powders and structurants increase the deodorant stick's hardness.

The present inventors have discovered that the water solubilities of certain components in the solid stick deodorant have great importance. Some deodorant ingredients will bring in moisture to the batch, which can solvate these components to different extents when the water evaporates and subsequently recondenses as free water in the batch. Certain batch processing conditions (such as a closed top on the tank) could more effectively trap this water in the tank, where it is then free to interact with components of the batch. For example, highly water soluble alkaline powders can contribute negatively towards natural and essential oil stability when dissolved. This is because many natural and essential oils contain a broad range of perfume chemicals, many of which can undergo degradation reactions when exposed to extreme pH or heat. This is why many natural and essential oils have shorter shelf lives than many commercial synthetic chemicals or perfumes. And certain antimicrobials may cause irritation due to high water solubility. Further, high water solubility can lead to grittier products as the more water soluble powders can agglomerate when exposed to moisture released from powders during the heat of manufacture.

Thus, embodiments of the present invention may include an antimicrobial with a low water solubility. An antimicrobial with a low water solubility may be, in some embodiments, an antimicrobial with a water solubility of at most 90 g/L at 25° C., in other embodiments at most 75 g/L at 25° C., or in still other embodiments at most 50 g/L at 25° C.

Materials with a water solubility above 90 g/L @25° C. include but are not limited to: potassium carbonate, potassium bicarbonate, sodium carbonate, sodium sesquicarbonate, triethyl citrate, and baking soda. Materials with a water solubility below 90 g/L @25° C. include but are not limited to: beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salycilic acid, phenoxyethanol, eugenol, linolenic acid, dimethyl succinate, citral, and triethyl citrate. Each of beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salycilic acid, phenoxyethanol, eugenol, linolenic acid, dimethyl succinate, and citral have a water solubility below 75 g/L @25° C., below 50 g/L @25° C., below 1 g/L @25° C., and below 0.2 g/L @25° C.

D. Antimicrobial Activity

Table 2 below shows the raw material microbial inhibition concentration data tested against two key underarm bacteria strains. As can be seen, the first three listed antimicrobials, lupamin, hexamidine, and piroctone olamine, perform particularly well against the bacteria as raw materials. Also performing well as raw materials are phenoxyethanol, eugenol, linolenic acid, dimethyl succinate, citral, triethyl citrate, and sepiwhite. Also performing moderately well against the bacteria as raw materials were magnesium carbonate/magnesium hydroxide and calcium carbonate.

TABLE 2

| Antimicrobial | C. mucofaciens | | S. epidermidis | |
|---|---|---|---|---|
| Lupamin | <2 | ppm | 4 | ppm |
| Hexamidine 36 mg/ml H2O | <2 | ppm | 7 | ppm |
| 100 mg/ml piroctone olamine in H2O | <5 | ppm | 10 | ppm |
| 100% Phenoxyethanol | 400 | ppm | 800 | ppm % |
| Eugenol 99% ETOH | 773 | ppm | 773 | ppm |
| Linolenic Acid 70% ETOH | 1093 | ppm | 1093 | ppm |
| Dimethyl Succinate 98% ETOH | 1531 | ppm | 3062 | ppm |
| Citral 96% ETOH | 1500 | ppm | 1500 | ppm |
| 100% Triethyl citrate | 1600 | ppm | 1600 | ppm |
| Sepiwhite 40 mg/ml H2O ins | 2000 | ppm | 1000 | ppm |
| Magnesium Carbonate & Magnesium Hydroxide 50 mg/ml H2O ins | >2500 | ppm | >2500 | ppm |
| Ca Carbonate 50 mg/ml H2O ins | >2500 | ppm | >2500 | ppm |
| Linoleic acid 100% ETOH | 3125 | ppm | 3125 | ppm |
| Conarom B (beta Bio) 100% ETOH | 3125 | ppm | 3125 | ppm |
| Hexyl Decanol 97% ETOH | 6062 | ppm | 3031 | ppm |
| Ajowan oil 50% ETOH | 12500 | ppm | 6300 | ppm |
| Oregano oil 50% ETOH | 12500 | ppm | 6300 | ppm |
| 100% Ethylhexyl glycerin | 12500 | ppm | 12500 | ppm |

TABLE 2-continued

| Antimicrobial | C. mucofaciens | S. epidermidis |
|---|---|---|
| Mineral oil 50% in ETOH | 12500 ppm | >50000 ppm |
| ACH 50% in H2O | 25000 ppm | 25000 ppm |
| NaCl 250 mg/ml H2O | >25000 ppm | >25000 ppm |
| Farnesol 95% ETOH | 47500 ppm | 5937 ppm |
| Phytol 97% ETOH | >49000 ppm | >49000 ppm |
| Nerolidol 98% ETOH | >49000 ppm | >49000 ppm |
| CaCl 500 mg/ml H2O | >50000 ppm | >50000 ppm |
| Isopropyl Myristate 98% ETOH | >59000 ppm | >59000 ppm |

While numerous antimicrobials exhibit efficacy against two main bacteria strains that antiperspirants and deodorants try to address, due to regulatory and safety reasons, there are sometimes limits as to how much of a particular antimicrobial may be put into an antiperspirant or deodorant formula. Therefore, there may be a need for multiple antimicrobials to work together in a formula to deliver enough long-term odor protection.

Deodorant Composition

The deodorant compositions as described herein can contain a structurant, an antimicrobial, a perfume, and additional chassis ingredient(s). The deodorant composition may further comprise other optional ingredient(s). The compositions can be in the form of a solid stick. The compositions may be free of dipropylene glycol, added water, castor wax, or any combination thereof. The compositions may be substantially free of or free of a substituted or unsubstituted 2-pyridinol-N-oxide material (piroctone olamine) The deodorant composition may be anhydrous. The deodorant composition may be free of added water.

Hardness

The deodorant compositions of the present invention may have a product or stick hardness from about 80 mm*10 to about 140 mm*10, as measured by penetration with ASTM D-1321 needle (see Hardness test method below). In some embodiments, the product hardness may be from about 80 to about 120 mm*10, and in others from about 85 to about 100 mm*10.

Perfume

Perfumes are often a combination of many raw materials, known as perfume raw materials. Any perfume suitable for use in a deodorant composition may be used herein. In some embodiments, the deodorant composition may be free of, or substantially free of a synthetic fragrance. A synthetic fragrance is one mostly derived through chemical synthesis where the starting material is no longer intact, but is converted to the new fragrance chemical.

A natural or essential oil fragrance is a result of natural sources wherein the fragrance material is not altered (chemically modified) but extracted from its natural source. These sources can include, but are not limited to, bark, flowers, blossoms, fruits, leaves, resins, roots, bulbs, and seeds. Natural or essential oils go through an extraction process instead of chemical synthesis. Extraction processes include, but are not limited to, maceration, solvent extraction, distillation, expression of a fruit peel, or effleurage.

Additional Chassis Ingredients

Starch

The deodorant composition may comprise a starch powder for dry feel or wetness absorption. Examples include but are not limited to arrowroot powder, tapioca starch, and corn starch.

Solvent

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Other Optional Ingredients

The anhydrous deodorant compositions of the present invention may further comprise any optional material that is known for use in antiperspirant and deodorant compositions or other personal care products, or which is otherwise suitable for topical application to human skin.

One example of an optional ingredient is a scent expression material. Scent expression or release technology may be employed with some or all of the fragrance materials to define a desired scent expression prior to use and during use of the deodorant products. Such scent expression or release technology can include cyclodextrin complexing material, like beta cyclodextrin. Other materials, such as, for example, starch-based matrices or microcapsules may be employed to "hold" fragrance materials prior to exposure to bodily-secretions (e.g., perspiration). The encapsulating material may have release mechanisms other than via a solvent; for example, the encapsulating material may be frangible, and as such, rupture or fracture with applied shear and/or normal forces encountered during application and while wearing. A microcapsule may be made from many materials, one example is polyacrylates.

Another example of optional materials are clay mineral powders such as talc, mica, sericite, silica, magnesium silicate, synthetic fluorphlogopite, calcium silicate, aluminum silicate, bentonite and montmorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, chelants, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Method of Making

The deodorant stick products of the present invention may be made by mixing all the components of the products in an open-top or vented tank. Many powders come with bound moisture, especially naturally high moisture powders like starches. In a mostly anhydrous process with waxes, melting the waxes above their melt point can release this bound water as the batch temperature increases. In a closed tank process this water vapor will condense in the tank and drip back into the batch as water. This water can interact with the most water soluble ingredients in the batch to have negative effects on the product, including releasing the pH of any antimicrobial ingredient, which can then degrade any perfume ingredients in the batch. Additionally, the condensed water can interfere with the wax and produce a stick softer than intended.

The present invention reduces the risk of these negative consequences. The ideal process remedy for this behavior is to produce the batches in one of four ways:

1. An open tank system where the water vapor can leave the batch tank to reduce or eliminate condensation.
2. A vented closed tank to also remove water vapor during the batch process.
3. A dual phase process where the moisture containing powders can be put into the cold phase separate from the wax phase which is heated. These two phases are then mixed before filling.
4. A low residence time batch process for a closed system, where the product has less than 3 hours residence time above 50° C. to reduce the rate of reaction from the moisture.

A method of making a deodorant composition or stick may comprise the steps of combining any of the herein described deodorant composition components in an open tank system or a vented closed tank. The components may be mixed, heated, and then cooled into a stick product. In some embodiments, the deodorant components may comprise at least about 40% of a liquid triglyceride, by weight of the composition, and an antimicrobial in an open tank system, heating the components, mixing the components, and cooling the components.

Test Methods

Hardness Test Method—Penetration Measurement for Deodorant Finished Products

The penetration test is a physical test method that provides a measure of the firmness of waxy solids and extremely thick creams and pastes with penetration values not greater than 250 when using a needle for D1321. The method is based on the American Society for Testing and Materials Methods D-5, D1321 and D217 and DIN 51 579 and is suitable for all solid antiperspirant and deodorant products.

A needle or polished cone of precisely specified dimensions and weight is mounted on the bottom of a vertical rod in the test apparatus. The sample is prepared as specified in the method and positioned under the rod. The apparatus is adjusted so that the point of the needle or cone is just touching the top surface of the sample. Consistent positioning of the rod is critical to the measured penetration value. The rod is then released and allowed to travel downward, driven only by the weight of the needle (or cone) and the rod. Penetration is the tenths of a millimeter travelled following release.

| APPARATUS | SUGGESTED TYPE (OR EQUIVALENT) |
| --- | --- |
| Penetrometer with Timer (see attached drawings Attachment 1 and Attachment 2) | Penetrometer Suitable For ASTM D-5 and D-1321 methods; Examples: Precision or Humboldt Universal Penetrometer (Humboldt Manufacturing, Schiller Park, IL USA) or Penetrometer Model PNR10 or PNR12 (Petrolab USA or PetroTest GmbH). |
| Penetration Needles | ANTIPERSPIRANT or DEODORANT SOLIDS can use: Needles as specified for ASTM Method D-5, NIST Certified, Fisher Scientific #01-512. Needles as specified for ASTM Method D 1321 /DIN 51 579, Officially certified, Taper-Tipped needle, No. H-1310, Humboldt Mfg. |

General Instructions—All Penetrometers—Keep the instrument and needles/probes clean at all times, free from dust and grime. When not in use, store needles in a suitable container to avoid damage. Periodic calibration should confirm:

Electronic Timer is correctly set. Verify against an independent stopwatch if unsure.

Shaft falls without visible signs of frictional resistance.

Ensure the total weight of the shaft and needle is 50±0.2 grams when the shaft is in free fall. Note: for modern, automated or digital systems this may be performed automatically and confirmed through annual calibration.

At time of use confirm:

Electronic Timer is correctly set to 5.0 seconds.

The appropriate needle is installed and is clean, straight and without obvious defects (visual inspection)

The penetrometer is level and the shaft is clean, straight and falls freely (visual inspection)

Once level, avoid shifting the position of the unit to maintain level.

Sample Preparation and Measurement

1. On a deodorant stick that has cooled ambiently to a temperature between 22° C. and 26° C. for at least 24 hours, slice off top ½ inch of product to achieve a flat surface with a wire cutter drawn across the upper lip of the canister.
2. For the first sample to be tested, lubricate the needle by gently wiping with a lint-free tissue coated with a small amount of the product to be tested. This small amount is typically taken from the shaved top.
3. Place the canister in the appropriate location for the measurement. Locate the sample so the needle will penetrate the product 9-11 mm from the inside of the canister wall on the long axis.
4. Using the coarse and fine adjustments, align the height of the penetrometer mechanism head so that the point of the penetrating needle is just touching the surface of the sample. A weak light at the side of the penetrometer which casts a shadow of the needle on the surface of the sample may be helpful in determining this contact. When a light area on the sample cannot be seen at the end of the tip of the needle's shadow, the needle height over the sample is correctly adjusted. The light should not be strong enough to heat or melt the sample surface. The needle should be just close enough to scratch the sample surface.
5. Perform the penetration measurement at this location by releasing the needle. Record the result.
6. Repeat Steps 2 through 4 at the other test point, i.e., at the other point 9-11 mm inside of the canister wall on the long axis.

To report results, units for penetration are tenths of a millimeter (1/10 mm=100 microns). For example, a result of 80 units is 80 mm*10 or 8 mm. Report the average results of at least 4 total measurements from 2 different sticks, report to the nearest tenth of a millimeter.

Tier 1 Anaerobic MIC Assay

The data in Table 2 above was generated with the following test method. The purpose of this assay is to determine if a compound or formulation has an antimicrobial effect in vitro.

It is understood that when not specifically noted in this procedure:

a) All materials, reagents and equipment required for this procedure are of appropriate design and condition of cleanliness and/or sterility as determined by their intended use.

b) The operator has been trained in aseptic technique and has been qualified to perform the procedure and accurately interpret the results.

c) All media required for this procedure was manufactured by a reputable commercial source egg. Difco, Merck etc. and has been stored and prepared as per manufacturer's instructions.

d) All routine laboratory controls, including but not limited to, media function and growth promotion tests, verification of sterility and use of positive and negative controls are being conducted.

Procedure: (All procedures performed in anaerobic chamber except where noted)

1. Apparatus

Incubator at 37° C.; 20-200 ul 12 channel pipette; 5-50 ul 12 channel pipette; 1250 ul 8 channel Thermo Scientific Matrix pipette; 96 well plate shaker (located in incubator); Beckman Coulter deep well cap mat #267005; Beckman Coulter deep 96 well plates #267007; Falcon 96 well tissue culture plates #353072; Vortexer; Culture tubes/caps Disposable sterile gloves; Sterile petri dishes; Standard microbiological lab equipment (sterile pipettes, syringes, tips, loops, etc.); Glass bottles/flasks for media; Autoclave; Parafilm; Spectrophotometer.

2. Media 0.9% or 0.85% saline solution
BHI agar supplemented with 1% Tween 80
BHI media supplemented with 1% Tween 80

3. Microbial Strains

*Staphylococcus epidermidis* (clinical isolate)
*Corynebacterium mucofaciens* (clinical isolate)

4. Test Procedure

Inoculum Preparation

Prior to testing streak organisms for isolation on BHI with 1% Tween 80 plates, wrap with parafilm and place in 37° C. incubator. When isolated colonies appear remove one representative colony from each plate and place each in 5 ml of BHI with 1% Tween 80 media. Incubate at 37° C. with shaking overnight. Inoculate 20 ml BHI with 1% Tween 80 (per 96 deep well plate to be tested) with 20 ul of the overnight culture (1-1000 dilution).

Master Plate Preparation

Compounds/formulations to be tested are diluted across a 96 deep well plate as shown below (for a 1% stock solution). 800 ul of 0.85% saline is added to wells A1 and B1 (as these will be the negative and positive control respectively). 800 ul each 1% stock solution+ positive control are added to wells C1 through H1. 400 ul 0.85% saline are added to all other wells. 400 ul is then removed from #1 well added to the #2 well and mixed. This is then continued across the plate resulting in a 50% dilution between wells across the plate (this can be easily accomplished with an automatic 8 channel Matrix pipette set to withdraw, dispense and mix).

|   | 1 | 2 | 3 | 4 | 5 | 6 |
|---|---|---|---|---|---|---|
| A | 800 ul saline | 400 ul NaCl | 400 ul NaCl | 400 ul NaCl | 400 ul NaCl | 400 ul NaCl |
| B | 800 ul saline | 400 ul NaCl | 400 ul NaCl | 400 ul NaCl | 400 ul NaCl | 400 ul NaCl |
| C | 800 ul + control | 400 ul NaCl | 400 ul NaCl | 400 ul NaCl | 400 ul NaCl | 400 ul NaCl |
| D | 800 ul compound 1 | 400 ul NaCl | 400 ul NaCl | 400 ul NaCl | 400 ul NaCl | 400 ul NaCl |
| E | 800 ul compound 2 | 400 ul NaCl | 400 ul NaCl | 400 ul NaCl | 400 ul NaCl | 400 ul NaCl |
| F | 800 ul compound 3 | 400 ul NaCl | 400 ul NaCl | 400 ul NaCl | 400 ul NaCl | 400 ul NaCl |
| G | 800 ul compound 4 | 400 ul NaCl | 400 ul NaCl | 400 ul NaCl | 400 ul NaCl | 400 ul NaCl |
| H | 800 ul compound 5 | 400 ul NaCl | 400 ul NaCl | 400 ul NaCl | 400 ul NaCl | 400 ul NaCl |
| A | Media Blank | Media Blank | Media Blank | Media Blank | Media Blank | Media Blank |
| B | Pos | Pos | Pos | Pos | Pos | Pos |
| C | 0.1 | 0.05 | 0.025 | 0.0125 | 0.00625 | 0.003125 |
| D | 0.1 | 0.05 | 0.025 | 0.0125 | 0.00625 | 0.003125 |
| E | 0.1 | 0.05 | 0.025 | 0.0125 | 0.00625 | 0.003125 |
| F | 0.1 | 0.05 | 0.025 | 0.0125 | 0.00625 | 0.003125 |
| G | 0.1 | 0.05 | 0.025 | 0.0125 | 0.00625 | 0.003125 |
| H | 0.1 | 0.05 | 0.025 | 0.0125 | 0.00625 | 0.003125 |

|   | 7 | 8 | 9 | 10 | 11 | 12 |
|---|---|---|---|---|---|---|
| A | 400 ul NaCl | 400 ul NaCl | 400 ul NaCl | 400 ul NaCl | 400 ul NaCl | 400 ul NaCl |
| B | 400 ul NaCl | 400 ul NaCl | 400 ul NaCl | 400 ul NaCl | 400 ul NaCl | 400 ul NaCl |
| C | 400 ul NaCl | 400 ul NaCl | 400 ul NaCl | 400 ul NaCl | 400 ul NaCl | 400 ul NaCl |
| D | 400 ul NaCl | 400 ul NaCl | 400 ul NaCl | 400 ul NaCl | 400 ul NaCl | 400 ul NaCl |
| E | 400 ul NaCl | 400 ul NaCl | 400 ul NaCl | 400 ul NaCl | 400 ul NaCl | 400 ul NaCl |
| F | 400 ul NaCl | 400 ul NaCl | 400 ul NaCl | 400 ul NaCl | 400 ul NaCl | 400 ul NaCl |
| G | 400 ul NaCl | 400 ul NaCl | 400 ul NaCl | 400 ul NaCl | 400 ul NaCl | 400 ul NaCl |
| H | 400 ul NaCl | 400 ul NaCl | 400 ul NaCl | 400 ul NaCl | 400 ul NaCl | 400 ul NaCl |
| A | Media Blank | Media Blank | Media Blank | Media Blank | Media Blank | Media Blank |
| B | Pos | Pos | Pos | Pos | Pos | Pos |
| C | 0.0015625 | 0.00078125 | 0.000390625 | 0.000195313 | 9.76563E-05 | 4.88281E-05 |
| D | 0.0015625 | 0.00078125 | 0.000390625 | 0.000195313 | 9.76563E-05 | 4.88281E-05 |

-continued

| | | | | | | |
|---|---|---|---|---|---|---|
| E | 0.0015625 | 0.00078125 | 0.000390625 | 0.000195313 | 9.76563E−05 | 4.88281E−05 |
| F | 0.0015625 | 0.00078125 | 0.000390625 | 0.000195313 | 9.76563E−05 | 4.88281E−05 |
| G | 0.0015625 | 0.00078125 | 0.000390625 | 0.000195313 | 9.76563E−05 | 4.88281E−05 |
| H | 0.0015625 | 0.00078125 | 0.000390625 | 0.000195313 | 9.76563E−05 | 4.88281E−05 |

Test Plate Preparation

In row A of a 96 deep well plate pipette 180 ul of sterile BHI with 1% Tween 80 as a negative growth control. All other wells receive 180 ul of inoculum. From the master plate introduce 20 ul to the corresponding row in the test plate using an 8-channel pipette. Loaded plates are placed on a plate shaker in the 37° C. incubator and incubated overnight. The next day read the O.D. 600 on a plate reader. The MIC is the last well from the right that has no bacterial growth.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

What is claimed is:

1. A deodorant stick comprising:
   a. at least about 25% of a liquid triglyceride;
   b. at least one antimicrobial; and
   c. a primary structurant with a melting point of at least about 50° Celsius; and
wherein said stick is free of an aluminum salt.

2. The deodorant stick of claim 1, wherein the antimicrobial is selected from the group consisting of baking soda, magnesium hydroxide, hexamidine, magnesium carbonate, zinc carbonate, thymol, magnesium hydroxide & magnesium carbonate hydroxide, sodium carbonate, magnesium carbonate hydroxide, partially carbonated magnesium hydroxide, calcium carbonate, polyvinyl formate, salicylic acid, niacinamide, cinnamon essential oil, cinnamon bark essential oil, cinnamic aldehyde and combinations thereof.

3. The deodorant stick of claim 1, wherein the antimicrobial is a powder with a water solubility of at most about 90 g/L at 25° C.

4. The deodorant stick of claim 1, wherein the deodorant stick is substantially free of baking soda.

5. The deodorant stick of claim 1, wherein the deodorant stick is substantially free of a synthetic fragrance.

6. The deodorant stick of any claim 1, wherein the deodorant stick is substantially free of silicones.

7. The deodorant stick of claim 1, wherein the deodorant stick comprises from 0% to 5% silicones.

8. The deodorant stick of claim 1, comprising at least about 35% of a liquid triglyceride.

9. The deodorant stick of claim 1, wherein the antimicrobial comprises baking soda.

10. The deodorant stick of claim 1, wherein the antimicrobial comprises magnesium hydroxide.

11. The deodorant stick of claim 1, wherein the stick comprises from about 8% to about 20% of the primary structurant.

12. The deodorant stick of claim 1, wherein the primary structurant has a melting point from about 50° C. to 75° C.

13. The deodorant stick of claim 1, comprising less than 5% of secondary structurants having a melting point above 60° C.

14. The deodorant stick of claim 1, wherein said stick comprises less than 8% of secondary structurants having a melting point of at least about 60° Celsius.

15. The deodorant stick of claim 1, wherein said stick has a hardness from about 80 mm*10 to about 140 mm*10, as measured by penetration with ASTM-D 1321 needle.

* * * * *